(12) United States Patent
Van Schaik

(10) Patent No.: US 6,681,635 B1
(45) Date of Patent: Jan. 27, 2004

(54) ACOUSTIC TRANSIT TIME MEASURING SYSTEM

(76) Inventor: Wilhelm Henricus Jurriaan Van Schaik, Mortelhof 2, Veldhoven (NL), 5502RG ( * ) Notice: Subject to any disclaimer, the term of this patent is extended or adjusted under 35 U.S.C. 154(b) by 0 days.

(21) Appl. No.: 09/719,555

(22) PCT Filed: Jun. 23, 1999

(86) PCT No.: PCT/NL99/00386
§ 371 (c)(1),
(2), (4) Date: Dec. 26, 2000

(87) PCT Pub. No.: WO99/67649
PCT Pub. Date: Dec. 29, 1999

(30) Foreign Application Priority Data

Jun. 24, 1998 (NL) .............................................. 1009485

(51) Int. Cl.⁷ ............................................. G01N 24/00
(52) U.S. Cl. ......................................... 73/597; 73/602
(58) Field of Search .................. 73/597, 644, 579, 73/599, 600, 602, 61.46, 61.47, 861.05, 659

(56) References Cited

U.S. PATENT DOCUMENTS

| | | | | |
|---|---|---|---|---|
| 4,022,058 A | * | 5/1977 | Brown | 73/861.28 |
| 4,285,241 A | * | 8/1981 | Smith et al. | 73/579 |
| 4,379,226 A | * | 4/1983 | Schiling et al. | 73/657 |
| 5,012,449 A | * | 4/1991 | Todd | 367/89 |
| 5,163,331 A | * | 11/1992 | Gill | 73/861.28 |
| 5,168,762 A | * | 12/1992 | Gill | 73/861.28 |
| 5,452,621 A | * | 9/1995 | Aylesworth et al. | 73/864.81 |
| 5,473,934 A | | 12/1995 | Cobb | 73/61.49 |
| 5,581,014 A | * | 12/1996 | Douglas | 73/24.01 |
| 5,627,323 A | * | 5/1997 | Stern | 73/861.28 |
| 5,650,571 A | * | 7/1997 | Freud et al. | 73/861.06 |
| 5,780,744 A | * | 7/1998 | Hall et al. | 73/597 |
| 5,783,745 A | * | 7/1998 | Bergman | 73/170.13 |
| 5,841,030 A | * | 11/1998 | Honsberg et al. | 73/579 |
| 5,852,233 A | * | 12/1998 | Arnold et al. | 73/105 |
| 6,092,419 A | * | 7/2000 | Dixon et al. | 73/602 |
| 6,293,136 B1 | * | 9/2001 | Kim | 73/19.03 |
| 6,314,380 B1 | * | 11/2001 | Seip et al. | 702/99 |
| 6,390,999 B1 | * | 5/2002 | Zscheile et al. | 604/4.01 |

FOREIGN PATENT DOCUMENTS

| | | |
|---|---|---|
| GB | 2130368 A | 5/1984 |
| GB | 2195767 A | 4/1988 |
| WO | WO96/29575 | 9/1996 |

OTHER PUBLICATIONS

U.S. 2002/0062681, Oxygen sensor and flow meter device, May 30, 2002.*
Matieson et al, Analytical Chemistry, vol. 44, No. 8, "Ultra–sonic Velocity in water–deuterium . . . ", pp. 1517–1520, Jul. 1972.

* cited by examiner

Primary Examiner—Hezron Williams
Assistant Examiner—Jacques Saint-Surin
(74) Attorney, Agent, or Firm—Jacobson Holman PLLC

(57) ABSTRACT

A method to determine a physical quantity within a measuring space by means of acoustic transit time measurement uses an acoustic transducer as a transmitter and an acoustic transducer as a receiver. The two functions can also be combined in a single transducer. The acoustic transit time measurement involves a time-dependent comparison between the shape of an acoustic transmitted signal selected at least partly on the basis of the type of signal processing to be used and at least two points in an acoustic received signal and/or a signal derived from that received signal again selected at least partly on the basis of the type of processing to be used. An apparatus for this method could be equipped with an acoustic signal-generating transducer, an acoustic signal detection transducer, a signal processing device which selects measuring points from the signal, and detection algorithm adapted to the shape of the signal.

11 Claims, 2 Drawing Sheets

ACOUSTIC TRANSIT TIME MEASURING SYSTEM

The invention involves a method to determine a physical quantity by means of acoustic transit time measurement using at least one acoustic transducer as a transmitter and at least one acoustic transducer as a receiver. The invention also includes an apparatus adapted to implement this method.

Such a method and such an apparatus have been described in WO93/0057. The apparatus described there uses acoustic transit time measurement to determine the temperature of a turbulent gas flow through a measuring space. It reduces the effects of noise on the measuring signal by using transmitted signals of a specific, selected frequency and aims to achieve a relatively accurate transit time measurement by means of the corresponding correlation operation. This method, however, is not sufficiently accurate for certain applications.

The present invention attempts, among other things, to overcome this limitation. For this purpose, a method of the type referred to above is characterised by a transit time measurement using an acoustic transmitted signal which is at least partly selected on the basis of the type of signal processing to be used, and at least two points in an acoustic received signal and/or a derived signal, which are also selected at least partly on the basis of the type of signal processing to be used.

Signal processing in order to determine the quantity to be measured involves determining the point in time at which the acoustic signal received shows the expected signal shape. This is achieved by applying a detection method to at least two specific points in the received signal. These points in the signal are representative of the shape of the relevant part of the acoustic received signal.

Since a known transmitted signal is used, and the transfer functions of the transducers and the medium are highly predictable, the detection system can make use of a relatively high level of prior knowledge of the expected received signal. This property, combined with the utilisation in the present invention of at least two points selected at least partly on the basis of the type of signal processing to be used in a received signal which is also selected at least partly on the basis of the type of signal processing to be used, allows considerable improvement of the accuracy of detection and hence of the accuracy of the transit time measurement.

The transmitted signal to be used is preferably selected at least partly on the basis of the geometry, the type of medium and other characteristics and features of the measuring space. In most cases, however, these characteristics solely, or at least largely, determine the frequency range of the transmitted signal, rather than, e.g., the frequency course of the transmitted signal, which means that this frequency course can be set to optimise the results. The accuracy of the transit time measurement can be improved by striving towards a large information content in the transmitted signal, the information content being adapted to the measurement path, the medium and the transducers. As a result of reflections, a known transmitted signal is received by the receiving transducer at the other end as a compound signal, which repeatedly includes the transmitted signal, whether or not distorted.

It should be noted that the transit time of an acoustic signal in a medium over a particular path can only be defined for a monochromatic signal and is then only valid for a homogeneous and isotropic medium in a stationary condition. In a compound signal, each frequency component has its own transit time for a particular path, since the frequency dependence of the velocity of sound results in velocity dispersion. Therefore, using a compound signal necessitates the use of weighted transit times.

In measuring particular physical quantities, such as temperature or distance, weighted transit times can be determined by means of algorithms which use information about the transmitted and detected signals and prior knowledge of other parameters. The functionality of the signal interpretation can be realised by means of algorithms based on operations such as filtering, correlating, interpolating, curve-fitting, statistical data processing and analysis in a time-frequency domain. Signal interpretation may result in a comparison function which yields, for each point in time, a measure of the similarity between the received signal and the transmitted signal or a signal derived from the latter.

In one preferred embodiment a weighted transit time of an acoustic signal is determined using knowledge consisting of models for the medium and/or the measuring space about the distortion which the signal undergoes on its path through the measuring space. This embodiment preferably uses an aperiodic transmitted signal, of limited duration, in order to reduce the influence of spatial reflections on the signal received. This allows highly accurate weighted transit time measurements for long measurement paths.

The knowledge required for signal generation and interpretation can be divided into initial knowledge, i.e., characteristics and features introduced into the system, and knowledge which changes during the process of measuring. The initial knowledge includes information on system data and system behaviour, parameterised models of the medium and the measuring space, and information on processes taking place in the medium. This initial knowledge is adapted on the basis of the changing process and environmental conditions, including changes in the measuring space, the measurement path and process conditions such as flow.

A further preferred embodiment is characterised by the fact that an acoustic signal, emitted by a transmitter, is acoustically reflected one or more times through the measuring space before being received by the receiver, which may or may not be the same as the transmitter. Thus, the transmitter and the receiver may be one and the same transducer. The transmitted signal is reflected through the measuring space by means of acoustic mirrors before being received by the same transducer, which now functions as a receiver. In addition to the advantage of requiring only one transducer, the use of reflection results in a fairly long measurement path even within a relatively small measuring space. This raises the accuracy of the local acoustic transit time measurement and reduces the influence of external factors such as the environmental temperature on the measuring system and hence on the transit time measurement, provided a suitable construction is used for the measuring system and the housing of the measuring space.

In a further preferred embodiment, the two points selected in a received signal are taken from the slope and the top of the signal, and are used for signal shape detection with the help of specially adapted signal processing based on combined slope and top detection of a received acoustic signal. If, for instance, analogue signal processing uses combined slope and top detection of a selected acoustic signal transmitted by a transmitting transducer, then the use of a transmitted signal selected on the basis of the in this case analogue signal processing technique and the two points in the received signal mentioned above allow detection with a relatively high level of selectivity and prior knowledge of the measuring signal. This results in a simple and extremely sensitive detection technique, unlike conventional signal level detection, in which a received signal, attenuated by damping, is detected at a different geometric part of the signal slope received. A well-known improvement of this latter technique is to repeat the measurement using adjusted amplification levels. The combined slope and top detection system applied in the present invention aims at shape detection based on knowledge of the signal shape, using slope detection as an indication of the expected signal top. The actual shape detection is implemented by determining the position of the signal top corresponding to the detected signal slope. Detection on the basis of the position of the signal top is quicker and invariant over time as regards signal attenuation.

Another preferred embodiment involves determination of the transit time of an acoustic signal by means of a method for calculating the time-dependent similarity between the shapes of two signals, which are derived whether or not according to models for the medium and measuring space from the transmitted and the received signal respectively. In particular, use is made of time-discrete calculation methods, based on a discrete model of the time-dependent similarity between the signals, using regression and numerical approximation methods to overcome the limitations of time-discrete calculation methods.

A further preferred embodiment uses a low-frequency transmitted signal to avoid loss of information within the acoustic path as a result of excessive damping over a long measurement path and/or reflections from geometric obstructions which are small relative to the wavelength of the acoustic signal used. The main advantage of the use of a low-frequency transmitted signal for long measurement paths is the reduced damping, as well as the fact that the signal, because of its larger wavelength, is not distorted by relatively small geometric obstructions in the acoustic path. In addition, the use of a transmitted signal with known frequency characteristics allows reduction of the measuring errors introduced by acoustic signal distortion by reflections and non-stationary phenomena within the measuring space and by Doppler-like phenomena resulting from transducer movement and/or inhomogeneous and/or non-stationary medium flow. The type of transmitted signal to be used is at least partly determined by the transfer functions in the signal path, including those of signal processors, the transducers and the medium to be investigated, as well as by obstructions in the measuring space and the geometry and other characteristics and features of the measuring space. This ensures that transmitted and received signals and signal processing are ideally suited to each other and allows the transmitted signal to be adapted to changing environmental and process conditions, thus improving the quality of data processing. Using the shape features of the transmitted signal with its known frequency characteristics makes it easy to take account of the signal s frequency distortion between transmitter and receiver. As was noted above, low-frequency signals with a relatively large information content are used, if possible, for longer measurement paths. This preferably involves the use of a relatively short sweep signal, i.e., a signal with a known, time-dependent, variable phase velocity.

Signals with a large power content and known information content are highly suitable for correlation techniques and can yield highly accurate results in real time from a single measurement, preferably using weighted correlation to measure transit time. A weighted correlation algorithm is employed to make optimum use of the information content of the received signal, while taking the transfer functions of the medium and the transducers into account. The acoustic transit time is determined with the help of correlation techniques by performing a cross-correlation between the transmitted signal or a signal derived from the latter and the received signal, with the position of the cross correlation top constituting a measure of the acoustic transit time.

In a further preferred embodiment, the resolution of the correlation operation determining the transit time of the acoustic signal is improved with the help of numerical approximation methods and curve-fitting, using a relevant, approximated section of the autocorrelation function of the transmitted signal or a signal derived from the latter based on prior knowledge of the shape of the correlation function, in order to determine accurately the position of the cross correlation top. A discrete transmission signal is derived from a predefined transmission signal, e.g. a sweep signal. In addition, a reference signal is defined as a discrete model of the signal at the receiving end, whose shape is as similar as possible to that of the measuring signal to be received, for the purpose of signal comparison. On the basis of this, a discrete autocorrelation of the reference signal therefore yields a function which can be assumed to be identical in shape to the cross correlation function obtained from the reference signal and the received measuring signal.

For the purpose of detection signal processing, the discrete autocorrelation function of the reference signal is directly fitted to the cross-correlation function by means of regression. The model is refined by oversampling the autocorrelation function of the reference signal and/or is described by a contour of the autocorrelation function, which is described by a Curve-Fitting model (C-F model). The C-F model is determined for a relevant portion of the function, which includes the correlation top. For this purpose, a continuous mapping is determined, interpolating the discrete correlation values. Thus, it constitutes a partial model of the correlation function which can be calculated a priori. The position of the top within the contour can be determined in advance by analytical or numerical means, after which it is available as a parameter value. This method offers much higher accuracy and resolution, as well as greater speed, than conventional signal processing based on correlation calculations and statistical data processing.

In practice, detection signal processing is achieved by calculating the cross correlation function using sample values determined at a relatively low sampling frequency. This means that the corresponding discrete correlation values are relatively far apart in time, precluding accurate top detection in the correlation function. The abovementioned contour of the C-F model, in which the position of the top is known, is used to fit the model to the calculated discrete correlation values by means of weighted regression analysis. This allows the ultimate position of the C-F model, positioned over the correlation values, to be determined with a high level of resolution, ensuring accurate determination of the position of the cross-correlation top. The C-F model, the parameter value for the position of the top in the model and the weight factors for the regression analysis are stored in the system as embedded knowledge.

In a further preferred embodiment, weighted transit times are determined accurately by means of a predefined signal distortion over a given measurement path, using models for the medium and the measuring space. The transmitted signal and the medium and measuring space models are used to define a reference signal, which is then used to determine the time-dependent similarity between the reference signal and the received signal.

In a further preferred embodiment, the time-frequency dependent similarity between the transmitted and received signals is determined by means of analysis in the Wigner domain or another time-frequency domain. The advantage of the Wigner domain over other time-frequency domains is that the former imposes no fundamental restrictions on the time and frequency resolutions. Its disadvantage is that its use results in cross terms between the various signal components.

In a further preferred embodiment, cross terms are eliminated by using a transmitted signal such that the Wigner transform of the reference signal itself contains no cross terms. In addition, the transmitted signal is chosen in such a way that if the reference signal occurs repeatedly in the received signal, the resulting cross terms can be filtered out. This can be achieved, for instance, by summing multiple points of the Wigner transform. The comparison function is obtained by summing multiple points of the Wigner transform, with the time components of the latter points relative to the time for which the value of the comparison function is computed.

In a further preferred embodiment, a physical quantity is determined by measuring, by acoustic or conventional means, one or more other quantities in a space in at least partially identical circumstances. In this context, conventional means determining a particular quantity on the basis of a measuring method which is in common practical use. The other quantities can be determined in the same measuring space and/or in a different measuring space, under certain identical conditions. If the behaviour of the other quantity is sufficiently known, a measurement which is in fact relative can still yield an absolute value. Alternatively, a physical quantity can be determined by using the invention to determine another quantity with the same signal processing method but over a different measurement path. For instance, humidity in a particular measuring space can be determined by combining a transit time measurement in that space with a similar transit time measurement in a different space containing a medium of known composition.

In a further preferred embodiment, analysis and elimination of the influence on the signal processing of the interaction between the shortest-path signal and its reflections in the measuring space is achieved by using the medium and measuring space models as well as the fact that in a stationary measuring space, the shortest path and the reflected paths will remain roughly unchanged. In identical circumstances of medium and temperature, transit times for different paths will depend on the lengths of the paths only, allowing accurate adaptive and statistical determination of the transit times for the various signal paths, and hence also the weighted transit time for the shortest-path signal, in measurements over a longer period of time involving a temperature course, which may be cyclic or otherwise.

With the help of prior knowledge and the corresponding models of the medium and the measuring space, information on partially redundant acoustic measurement paths can be used to determine a particular quantity over a section of an acoustic measurement path. This allows the use of acoustic tomography, as described for instance in GB 2235294-A. This can be achieved not only with fixed transducers, but also with a system of transducers in linear or rotary motion, whether or not using one and the same transducer for transmission and reception.

One preferred embodiment of the invention is an apparatus fitted with an acoustic transducer for signal generation, an acoustic transducer for signal detection, a signal processing unit which selects at least two measurement points and a signal processing unit which processes a measuring signal transmitted by a transmission transducer. In particular, the apparatus is fitted with one or more acoustic mirrors which fold the measurement path.

A further embodiment of such an apparatus is fitted with a measuring-point selecting device which locates measuring points in a transmitted signal, coupled with a signal detection device allowing combined signal top—signal slope detection.

Some examples of the invention are described in greater detail below, with reference to the following drawings.

Figure 1:
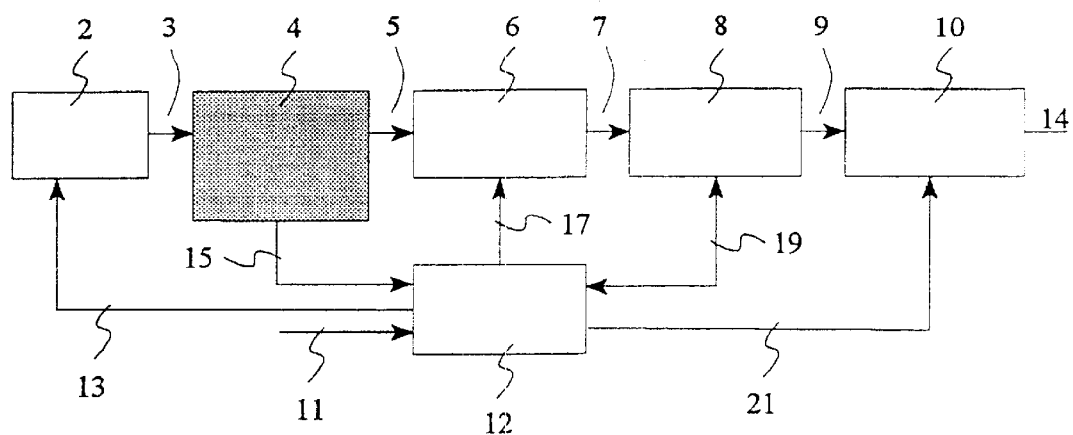
FIG. 1 is a block diagram of a measuring system based on the invention.

A measuring system like that shown in FIG. 1 includes an acoustic transmitter (2), a measuring chamber (4), a signal receiver (6), a signal processing unit (8), a measurement data processing unit (10) and a knowledge unit (12).

The intelligent, adaptive knowledge and control unit of the knowledge-based and rule-based measuring system, which contains knowledge and instructions, is referred to for short as the knowledge unit (12) and contains a discrete model of a signal to be transmitted. This signal is passed via a conduit (13) to the transmitter (2), where it is converted into an acoustic signal. The latter signal s transferred to the medium in the measuring chamber (4) via a conduit (3). After traversing the medium, the acoustic signal, now distorted and supplemented by undesirable reflections, is transferred to the signal reception unit (6) via a conduit (5).

The knowledge unit (12) also contains models of the measuring medium and the measuring chamber, which describe the influences the signal undergoes along the measurement path, allowing the acoustic signal distortion and the reflections to be predicted. The measuring chamber model describes the impact of the geometric aspects of the measuring chamber on the propagation of the sound in the chamber. The medium model describes the characteristics of the medium within the measuring chamber as regards the propagation of sound, insofar as these relate to signal distortion in the acoustic path. Additional model parameters required to determine the quantity to be measured, such as relative humidity and $CO_2$ content, are passed to the knowledge unit (12) from the measuring chamber (4) via a conduit (15). The parameters for the models, as well as the shape of the transmitted signal, are passed to the knowledge unit via a conduit (11) at the start of the procedure.

The shape of the transmitted signal, the models and the parameters for these models are passed by the knowledge unit (12) to the signal processing unit (8) via a conduit (19), in order to be processed. The signal processing unit uses these data to predict the shape of the acoustic signal to be received. The shape of the received signal passed by the receiver (6) via a conduit (7) to the signal processing unit (8) is now compared in a discrete manner with the shape of the predicted signal, yielding a comparison function. The maximum of the comparison function between the model and the processed received signal produced in the signal processing unit represents the transit time of the acoustic signal. Since the shapes are compared in a discrete manner, the above-mentioned comparison function is also discrete in nature. The desired maximum in the function will, however, usually not coincide with a discrete sampling point, which means that the resolution with which the transit time can be determined is limited by the sampling interval selected. Therefore, the discrete comparison between the shapes is performed using oversampled signals. This results in a smaller sampling interval, increasing the transit time resolution.

Additional improvement can be achieved by obtaining in advance a model of the comparison function; this can be done by comparing the predicted signal with itself. Curve-fitting can be used to produce a continuous model of the top of the signal. If this continuous model is superimposed on the discrete comparison function obtained by comparing the actually received signal with the predicted received signal, the position of the top can be determined even more accurately. A relevant section of the comparison function is converted into a continuous function by means of curve-fitting. The model of the continuous function is then fitted by means of curve-fitting to the comparison function resulting from the measurement, which was derived from the predicted and measured received signals. This procedure allows the weighted acoustic transit time to be determined very accurately.

Measuring chamber-dependent parameter settings are passed to the receiver (6) via a conduit (17). The knowledge unit (12) shows adaptive behaviour and communicates interactively with the signal processing unit (8) via a conduit (19). On the basis of the rough values for the shortest acoustic measurement path and the reflection paths, which are entered via a conduit (11), the signal processing unit, in interaction with the knowledge unit, determines the weighted transit time of the shortest-path signal during the signal processing, using approximation based on the temperature variations occurring during the measurement process.

Under equivalent circumstances of temperature and medium composition, the transit times for the shortest-path and indirect-path signals show a distance-dependent relationship. The maxima of the signal comparison functions corresponding to the various acoustic paths shift if the temperature in the measuring chamber changes over time. These shifts are used to help determine the shortest acoustic path and the reflected paths, using the estimated initial values as the basis of the heuristic, calculation-based search program. Using the knowledge of the measuring signals obtained in the measuring process, the signal processing unit (8) composes a new transmission signal, adapted to the changed process conditions, as well as new comparative functions, which are stored in the knowledge unit (12) for use in subsequent measurements. Knowledge rules and parameters from the measuring chamber model are passed to the measurement data processing unit (10) via a conduit (21), while the signal processing unit (8) passes the weighted acoustic transit time to the measurement data processing unit (10) via a conduit (9). The measurement data processing unit uses these data to calculate the value of the physical quantity to be determined and exports this value through a conduit (14).

Figure 2:
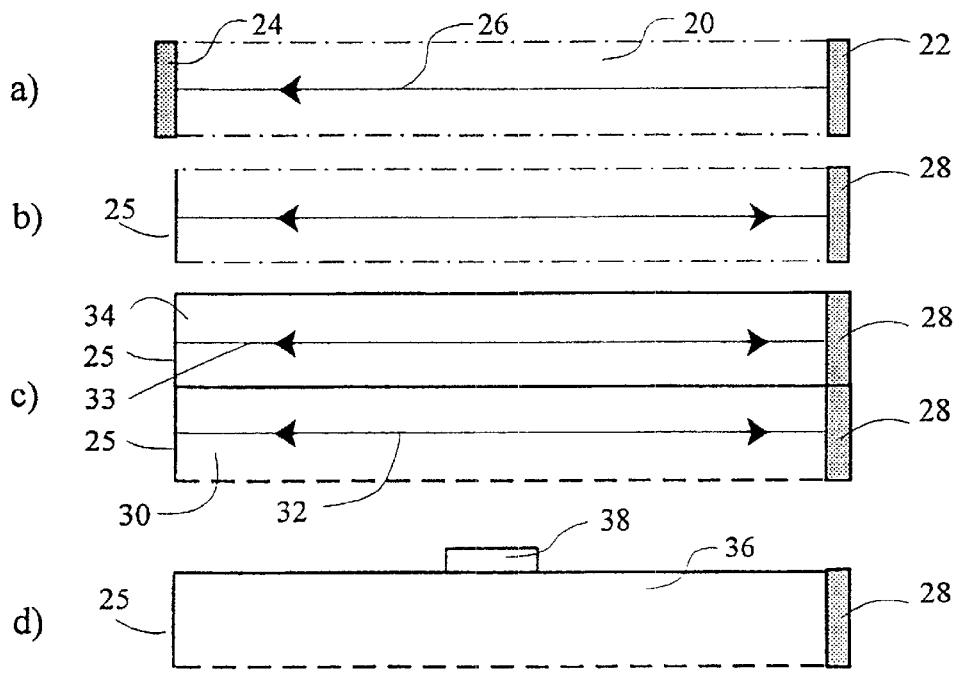
FIG. 2 is a diagram showing some embodiments of measuring systems based on the invention.

FIG. 2a shows a measuring chamber (20) in its simplest version, with an acoustic transmitter (22) at one end and an acoustic receiver (24) at the opposite end. An acoustic signal traverses the measuring chamber via a particular path (26). The apparatus can determine, for instance, the temperature, humidity, gas or liquid composition, etc., in the chamber. In principle, only relative measurements are possible, but these can be converted into absolute values using known references. In FIG. 2b, the receiver has been replaced by an acoustic mirror (25), and the transmitter (28) also functions as an acoustic mirror and as the receiver. This extends the measurement path within the same space by a factor of 2 or a multiple of this, with the relative accuracy of the transit time measurement increasing proportionally.

FIG. 2c shows a set-up which includes not only the actual measuring chamber (30) for a particular measurement path (32), but also a reference chamber (34) whose temperature conditions mimic those of the actual chamber as closely as possible. If the reference chamber is filled with a medium of known composition, direct absolute measurements can be performed for both the measurement path (32) and a measurement path (33).

FIG. 2d shows a measuring chamber set-up (36) in which the reference measuring chamber for temperature measurements has been replaced by a temperature detector (38). This allows the set-up to be used for direct measurements of, e.g., humidity or the composition of a gaseous mixture.

Figure 3:
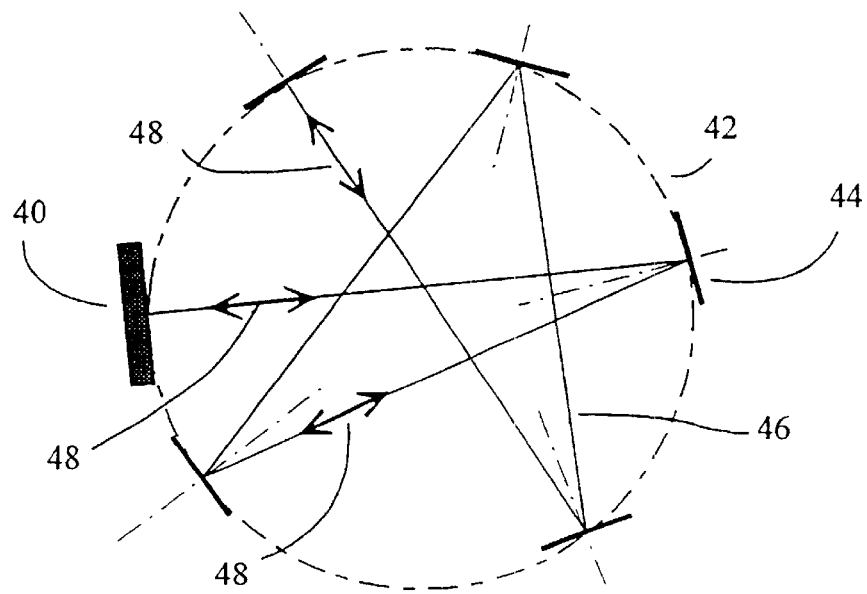
FIG. 3 shows an example of a measuring system with folded measurement path.

A measuring chamber of the type shown in FIG. 3 includes one single transducer (40) which functions as both transmitter and receiver. Acoustic mirrors (44) are mounted within the measuring chamber, at a virtual boundary (42), creating a relatively long measurement path (46) within a relatively small measuring space. The virtual boundary marked by the mirrors defines a subspace within the measuring space, allowing local measurements to be performed. The acoustic temperature measuring method allows accurate temperature measurements virtually in real time. The arrows (48) indicate the path of the measuring signal. A 1 meter measurement path can give rise to an accuracy of 0.01 Kelvin, provided the rate of thermal expansion of the partition on which the acoustic mirrors have been mounted is low or its effect is compensated for in the measured value.

Figure 4:
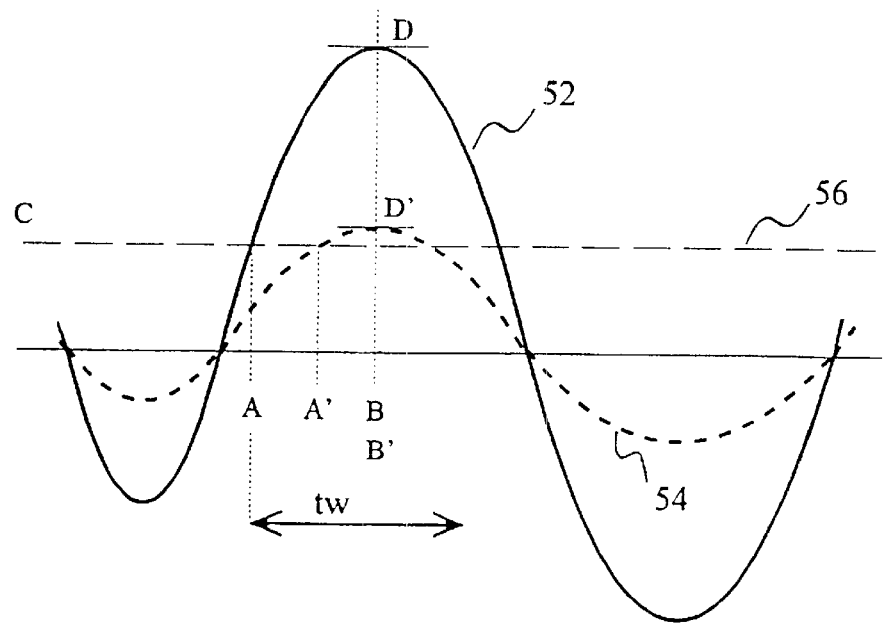
FIG. 4 shows an example of a measuring signal which can be used in measuring systems based on the invention.

FIG. 4 shows acoustic received signals (52, 54) emitted by the transmitter and received by receivers situated at different distances from the transmitter. Compared to signal (52), signal (54) is more attenuated, since it has traversed a longer path through the medium, resulting in greater damping.

Signal detection is performed on the basis of a combination of various interrelated relevant points in the signal. The combined detection consists of a signal level detection (56), which is used as a predetection distinguishing the actual signal from environmental influences, followed by top detection within a time window tw.

To illustrate the timing aspect, the two received signals (52 and 54) have been superimposed. For this purpose, signal (54) has been shifted in time and superimposed on signal (52), with the level detection (56) applied to both. The level detection occurs at time A for signal (52) and at the shifted time A for signal (54). Using this combined detection with level detection (56), it can be concluded that the detection of a top within a time window tw after the moment of the level detection indicates that the transmitted signal has been detected at times B and B respectively. This means that both signals are detected at the same point in time, relative to the start of the signal. The time window tw is determined by the frequency of the transmitted signal and the speed of sound in the medium. The time window is such that it includes all characteristic points of the signal which are needed for the combined detection. The advantage of the present detection method is that detection always takes place at the same, amplitude-independent relative point during the signal, independent of the signal s attenuation.

The shape of the transmitted signal is chosen in such a way that it takes account of the distortion which is to be expected over the measurement path in a particular medium. The advantage is that fewer processing steps have to be applied to the received signal, allowing the transit time measurement to be quicker and more accurate.

What is claimed is:

1. A method for determining a physical quantity within a measuring space by use of acoustic transit time measurement, using at least one acoustic transmitting transducer and at least one acoustic receiving transducer, comprising the steps of:

transmitting an acoustic signal;

selecting said acoustic signal at least partly on a type of signal processing and detection of at least two points in an acoustic received signal and/or a signal derived from that received signal again selected at least partly on the basis of the type of processing to be used, the at least two points being situated respectively on the slope and at the top of said acoustic received signal being used for combined signal top-signal slope detection with the aid of a specifically adapted signal processing technique.

2. The method as claimed in claim 1, further comprising the step of:

determining a weighted transit time of the acoustic signal using prior knowledge, wherein said prior knowledge including models for a medium and/or measuring space, and said prior knowledge being a distortion to which the signal is subjected within the measuring space.

3. The method as claimed in claim 1, comprising the step of calculating the transit time of the acoustic signal with the help of a method which determines a time-dependent similarity between two signals, which have been derived whether or not using medium and measuring space models from the received and transmitted signal respectively.

4. The method as claimed in claim 3, further comprising the step of using an analysis in a time-frequency domain to calculate the time-dependent similarity between two signals, for estimating the transit time of an acoustic signal.

5. The method as claimed in claim 3, further comprising the steps of using time-discrete calculation methods based on a model of the time-dependent similarity between two signals, and using regression to fit the model to the time-discrete similarity between the signals to avoid the limitations of time discrete methods.

6. The method as claimed in claim 1, further comprising the step of using a low-frequency transmitted signal to avoid loss of information over the acoustic path as a result of excessive damping over a long measurement path and/or reflection from geometric obstructions which are small relative to the wavelength of the acoustic signal used.

7. The method as claimed in claim 1, further comprising the step of using a transmitted signal with characteristic, pre-known, time-dependent frequency course to reduce measuring errors arising from acoustic signal distortion due to reflections and non-stationary phenomena within the measuring space.

8. The method as claimed in claim 1, further comprising the step of:

determining a physical quantity within a measuring space based on other quantities using the same or a different measuring technique over a different measurement path under partially equal conditions.

9. The method as claimed in claim 1, further comprising the step of:

determining weighted transit times with a signal processing technique based on medium and measuring space models and sound velocity changes within the measuring space, which may or may not be cyclic, assuming constant acoustic signal paths and invariant medium conditions.

10. A method for determining a physical quantity within a measuring space by use of acoustic transit time measurement, using at least one acoustic transmitting transducer and at least one acoustic receiving transducer, comprising the steps of:

transmitting an acoustic signal by said at least one acoustic transmitting transducer wherein said acoustic signal being reflected through the measuring space one or more times via acoustic reflection before being received by said at least one acoustic receiving transducer;

selecting said acoustic signal at least partly on a type of signal processing and detection of at least two points in an acoustic received signal and/or a signal derived from that received signal again selected at least partly on the basis of the type of processing to be used.

11. A method for determining a physical quantity within a measuring space by use of acoustic transit time measurement, using at least one acoustic transmitting transducer and at least one acoustic receiving transducer, said method comprising the steps of using signal processing based on a comparison in a discrete manner between a) a predicted distorted acoustic signal transmitted through said space, based on models for the medium and measuring space concerning the distortion to which the signal is subjected within the measuring space and on the transmitted signal, and b) an actual measured acoustic signal transmitted through said space to determine the acoustic transit time, and using at least two selected points located on a slope and at a top of the received acoustic signal respectively, the at least two selected points being used for combined signal top-signal slope detection with the aid of a specially adapted signal processing technique.

* * * * *